United States Patent [19]
Terhune et al.

[11] Patent Number: 5,426,678
[45] Date of Patent: Jun. 20, 1995

[54] METHOD FOR ULTRASONIC INSPECTION OF A CLOSELY PACKED ARRAY OF FUEL RODS SURROUNDED BY A THIN-WALLED METALLIC CHANNEL

[75] Inventors: James H. Terhune; David L. Faulstich, both of San Jose, Calif.

[73] Assignee: General Electric Company, San Jose, Calif.

[21] Appl. No.: 92,099

[22] Filed: Jul. 16, 1993

[51] Int. Cl.⁶ .................................................. G21C 17/00
[52] U.S. Cl. .................................... 376/252; 376/249; 73/861.25
[58] Field of Search ............... 376/252, 249, 247, 250; 73/861.25

[56] References Cited

U.S. PATENT DOCUMENTS

| | | | |
|---|---|---|---|
| 3,919,881 | 11/1975 | Metherell | 73/67.5 H |
| 4,025,166 | 5/1977 | Felstead | 350/161 |
| 4,126,514 | 11/1978 | Wonn | 376/252 |
| 4,443,402 | 4/1984 | Marini et al. | 376/252 |
| 4,565,088 | 1/1986 | Crambes | 73/61.1 R |
| 5,118,464 | 6/1992 | Richardson et al. | 376/252 |
| 2,541,497 | 1984 | France (Foreign French report) | ...X |

OTHER PUBLICATIONS

Krautkramer, J., et al., "Ultrasonic Testing of Materials", 4th fully revised Edition, pp. 244, 581,607, (1990).
J. Sound & Vibration, "Transmission of Sound Through an Array of Scatterers", Mungur and Fahy, Vol. 9, No. 2, pp. 287-294 (1969).
Kernenergie, "Development of Computed Tomographic Methods for Verification of Nuclear Materials in Storage etc.", Levai, Vol. 32, No. 2, pp. 50-57 (1989). Not provided.

*Primary Examiner*—Donald P. Walsh
*Assistant Examiner*—Meena Chelliah
*Attorney, Agent, or Firm*—J. E. McGinness

[57] ABSTRACT

A method for ultrasonically inspecting a closely packed regular array of mutually parallel, uniformly sized and spaced rigid rods surrounded by a thin-walled metallic channel and immersed in a compressible medium. The method utilizes the properties of coherently scattered ultrasonic waves to identify rods which are defective, out of position or missing. A plane, monochromatic ultrasonic wave is transmitted toward the array of rods on one side thereof. Then an interference pattern produced on an opposing side of the array is detected. This interference pattern is the result of multiple scattering and diffraction of the plane ultrasonic wave during propagation through the array of rods. When the wavelength is comparable with the rod diameter and the rods are not too close together, scattering results in spatial relationships that produce an unusually large amount of wave penetration through the array in certain directions relative to the incident propagation vector. This is akin to Bragg scattering and is dependent on direction, wavelength, and details of the cylindrical array dimensions.

14 Claims, 7 Drawing Sheets

METHOD FOR ULTRASONIC INSPECTION OF A CLOSELY PACKED ARRAY OF FUEL RODS SURROUNDED BY A THIN-WALLED METALLIC CHANNEL

FIELD OF THE INVENTION

This invention generally relates to nondestructive examination of components of a nuclear power plant. In particular, the invention relates to ultrasonic inspection of the components of the fuel core of a nuclear reactor.

BACKGROUND OF THE INVENTION

Figure 1:
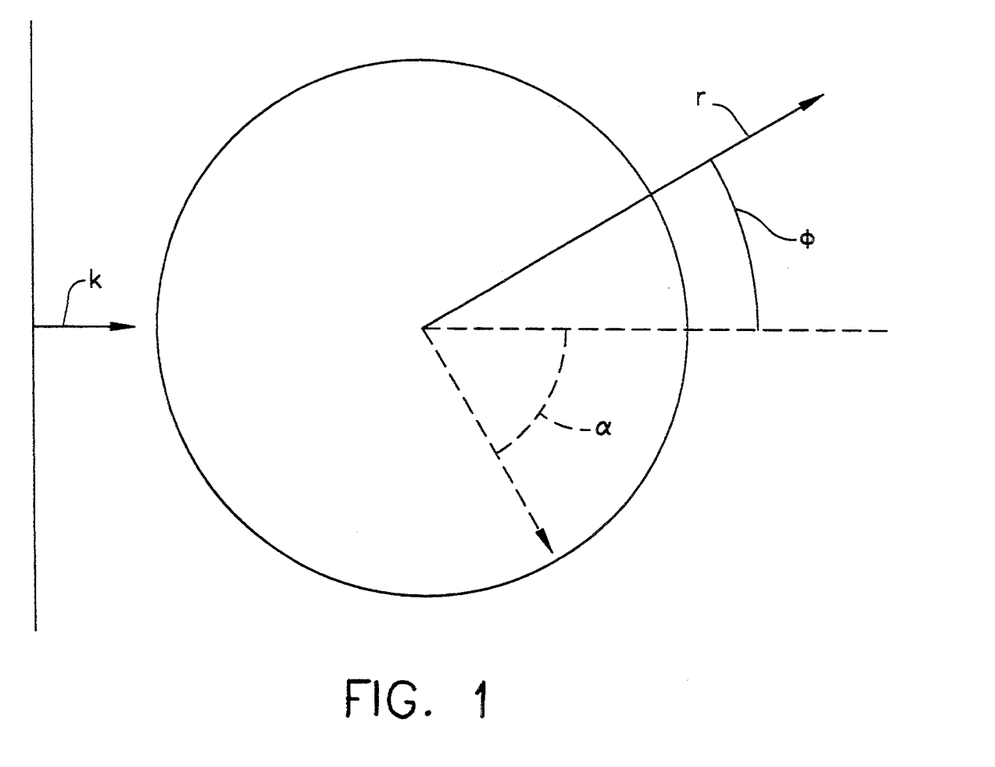
FIG. 1 is a diagram depicting a plane ultrasonic wave impinging on a long rod.

Consider a long rod of radius $a$ impacted by a plane wave of intensity $I_0$ and frequency $\omega$ traveling perpendicular to the rod axis, as depicted in FIG. 1. The spatial part of the wave pressure, $p_i$, can be expanded in cylindrical harmonics as:

$$p_i = P_0 \sum_{m=0}^{\infty} i^m \epsilon_m J_m(kr)\cos(m\phi) \quad (1)$$

where:

$$P_0 = \sqrt{\rho c I_0} \; ; \; k = \frac{\omega}{c} \; ; \; \epsilon_m = \begin{cases} 1; m = 0 \\ 2; m > 0 \end{cases} \quad (2)$$

$\rho$ is the fluid density and $c$ is the sonic velocity in the fluid. The radial velocity $u_i$ corresponding to the plane wave expansion is:

$$u_i = \frac{1}{i\omega\rho} \frac{\partial p_i}{\partial r} = \frac{P_0}{i\rho c} \sum_{m=0}^{\infty} i^m \epsilon_m J'_m(kr)\cos(m\phi) \quad (3)$$

The effect of a rod with its axis located at $r=0$ is to distort the incoming plane wave, thereby inducing a scattered outgoing wave of a size and shape sufficient to meet the zero radial velocity boundary condition at the rod surface:

$$u_i(ka) = -u_s(ka) \quad (4)$$

where the scattered wave radial velocity $u_s$ is:

$$u_s = \frac{1}{i\omega\rho} \frac{\partial p_s}{\partial r} = \frac{1}{i\rho c} \sum_{m=0}^{\infty} A_m H'_m(kr)\cos(m\phi) \quad (5)$$

and the scattered wave pressure $p_s$ is:

$$p_s = \sum_{m=0}^{\infty} A_m H_m(kr)\cos(m\phi) \quad (6)$$

The Hankel function of the first kind:

$$H_m(kr) = J_m(kr) + iY_m(kr) \quad (7)$$

is descriptive of outgoing waves, valid for $r \geq a$. The boundary condition (4) requires:

$$\sum_{m=0}^{\infty} \{P_0 i^m \epsilon_m J'_m(ka) + A_m H'_m(ka)\}\cos(m\phi) = 0 \quad (8)$$

which must be satisfied term-by-term. Therefore:

$$A_m = -P_0 i^m \epsilon_m \frac{J'_m(ka)}{H'_m(ka)} \quad (9)$$

The ratio of the derivatives results in a complex function of $ka$, which can be written as:

$$A_m = -P_0 i^{m+1} \epsilon_m e^{-i\gamma_m} \sin(\gamma_m) \quad (10)$$

where:

$$\gamma_0 = -\tan^{-1}\left[\frac{J_1(kc)}{Y_1(kc)}\right] \quad (11a)$$

$$\gamma_m = -\tan^{-1}\left[\frac{J_{m-1}(kc) - J_{m+1}(kc)}{Y_{m+1}(kc) - Y_{m-1}(kc)}\right] \quad (11b)$$

These phase shifts are the key to the behavior of the scattered wave and, therefore, to the total intensity pattern of the ultrasonic field.

The total field intensity is given by:

$$I(r,\Psi) < \tfrac{1}{2} Re\{p_t u_t^*\} = \tfrac{1}{2} Re\{[p_i+p_s][u_i+u_s]^*\} \quad (12)$$

where the factor of $\tfrac{1}{2}$ is due to a time-average over a period of the wave. Evidently, computation of the phase shifts allows calculation of the total intensity as a function of spatial position relative to the axis of the rod. The direction $\Psi=0$ is defined to be that of the incoming wave propagation vector, as shown in FIG. 1.

Figure 2:
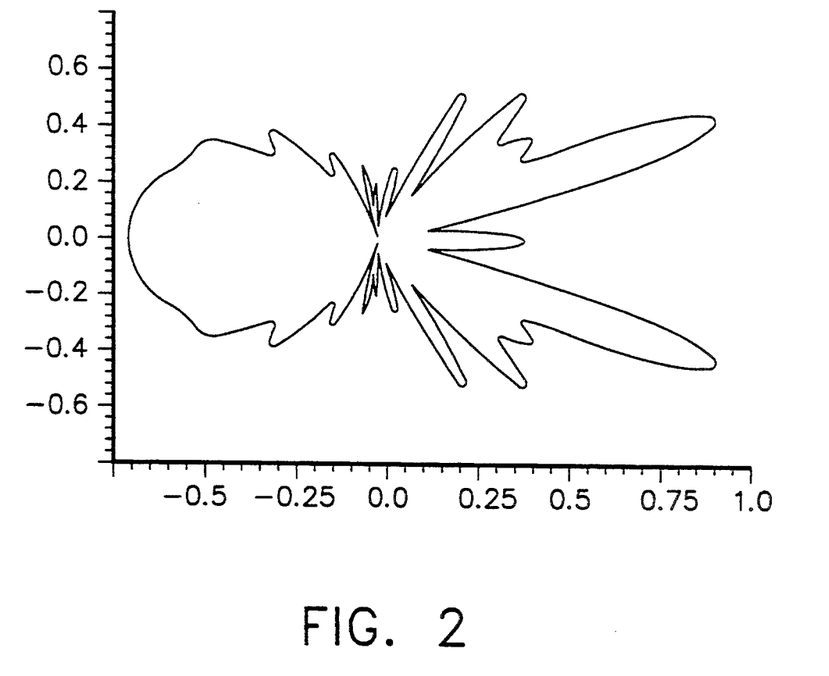
FIGS. 2 and 3 are polar plots of the normalized total intensity and normalized scattered intensity, respectively, for an incident ultrasonic wave impinging on a rod.

The normalized total intensity for a frequency of 213.2 kHz, a rod radius of 6.13 mm and a field radius of 23 mm ($ka=5.3$, $kr=31.4$) is shown in a polar plot in FIG. 2. The incident wave propagates from left to right along the axis of symmetry. The rod axis is perpendicular to the plane of the page and is centered at the origin.

The back-scatter is roughly isotropic, the side-scatter is small, and the forward-scatter has symmetrical lobes, the largest of which are centered at about $\pm 25°$ from the X axis. A significant amount of energy is scattered along the (forward) X axis. The oblique forward and back lobes are the result of edge diffraction from the circumference of the rod. The on-axis back lobe is the specular reflection signal, and the on-axis forward lobe results from incomplete interference effects from the edge diffraction.

Figure 3:
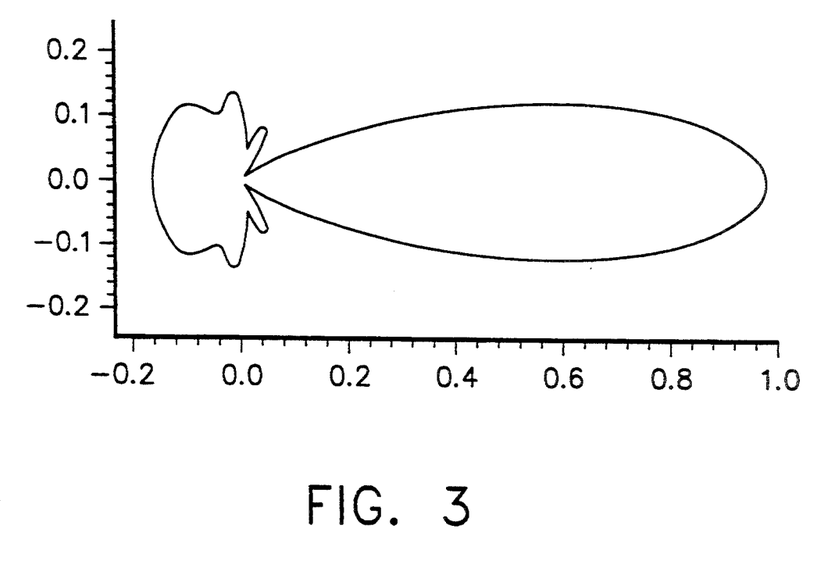

A significant amount of energy diffracts around the rod and is redistributed in polar angle, accounting for the forward lobes. This can be understood by examining the scattered wave intensity shown in FIG. 3. Note the broad forward lobe that interferes with the incoming plane wave to form the structured pattern of the total intensity. The back-scatter is rather isotropic, but lower in magnitude than the forward scatter.

Other cases of potential interest exist for different frequencies and rod parameters. The lower frequencies tend to broaden the forward lobes, increase the amplitudes of the diffracted waves and slightly reduce the forward peaking. The higher frequencies have the opposite effects. The complexity of the total field increases with frequency. Structure in the back-scatter increases as more energy is diffracted forward to further interfere with the incident wave. The oblique forward and back lobes are similar to diffraction rings from the cylinder outer edges. The scattered intensity is more peaked forward, and the lobes are more numerous for the higher frequencies.

The case of two or more rods is much more complex than that of an isolated rod, not only because of the boundary conditions, but also because of the issue of coherence. If two widely separated rods are excited by a plane wave impacting each at different times, they scatter the incident energy independently, in general. The resulting field is a superposition of the individual scattered waves, and the intensity is roughly proportional to the algebraic sum of the individual intensities at any particular point. This is also the case when the scatterers are small and fairly closely spaced, but occupy a region of space large compared to the wavelength.

In certain directions, the scattered waves add in phase; in other directions, destructive interference occurs, either partially or totally. This depends on the center-to-center spacing of the rods, as well as their radius and the distance of each from the field point. Furthermore, the time at which each is impacted by the plane wave should be very nearly the same to establish temporal coherence.

In the long wavelength limit, the rods are excited simultaneously. This is not true, in general, for wavelengths comparable with the rod spacing, since the waves travel at the velocity of sound c. The time-of-flight between scattering centers becomes significant in this case, generally destroying coherence. The result is incoherent, or diffuse, scattering in the case of N individual scatterers, and the intensity is proportional to N. Incoherent scattering is quite isotropic for a large number of randomly sized and spaced scatterers.

The scatterers may be arranged in a regular pattern, or array, that is large compared to the wavelength, but having a spacing and radius that is small compared to the wavelength. In this case, coherent scattering may occur in which the intensity in certain directions is proportional to $N^2$. This is due to a cooperative portion of the scattered waves, in which each individual scatterer adds its contribution to the total wave amplitude in phase. The rest of the scattered intensity is incoherent and appears as a diffuse background radiation. However, because of the long wavelength, no information is available regarding any individual scatterer. In fact, the familiar case of coherent x-ray scattering by crystals yields information about the crystal structure (planar spacing, etc.), but very little else.

SUMMARY OF THE INVENTION

The present invention is a method for ultrasonically inspecting a closely packed array of fuel rods surrounded by a thin-walled metallic channel. The method utilizes the properties of coherently scattered ultrasonic waves to identify fuel rods which are defective, out of position or missing, especially in reconstituted fuel bundles.

When a plane, monochromatic ultrasonic wave strikes an obstacle in its path, some of the wave is deflected from its original direction in a scattered wave. The total outgoing wave is the vector sum of the incident and scattered waves, spreading out from the obstacle in all directions. The scattered wave re-radiates the incident energy, resulting in an angular dependence of intensity similar to an antenna pattern.

In the case of a cylinder scattering ultrasound whose wavelength is of the same order as the cylindrical radius, most of the scattered wave travels in a direction different from the incident wave. A fraction of the incident wave diffracts around the cylinder and interferes with the scattered wave to form an ill-defined shadow zone, and some of the incident wave interferes with the back-scattered wave to form a reflection zone in front of the obstacle. At the off-angles, a relatively complicated radiation pattern exists, which contains a significant amount of the incident energy, or intensity. In particular, the circumference of the cylinder radiates lobes that are especially intense in the forward direction.

The interaction of a plane wave with a regular array of uniformly sized and spaced cylinders immersed in a compressible medium, such as water, is an example of multiple scattering. When the rod spacing is small compared to the ultrasonic wavelength, it is found that little of the incident wave penetrates through the array, almost all of it being reflected at the first row of cylinders. However, when the wavelength is comparable with the rod diameter and the rods are not too close together, scattering results in spatial relationships that produce an unusually large amount of wave penetration through the array in certain directions relative to the incident propagation vector. This is akin to Bragg scattering, well-known in x-ray and neutron diffraction, and is dependent on direction, wavelength, and the details of the cylindrical array dimensions.

When one considers an idealized reactor fuel bundle as a regular array of uniform, rigid rods completely immersed in water, Bragg scattering presents a means of inspecting the bundle for leaking or missing rods and nonuniformity of rod spacing. The fuel channel surrounding the bundle readily transmits ultrasound, which then penetrates the square lattice of rods, provided there is nothing to prevent or impede the scattering process. Such an impediment might consist of radioactive gas bubbling out of a cracked rod that locally perturbs the acoustic impedance, thereby disrupting at least part of the scattering process. In addition, if a leaking rod swells or otherwise changes shape, then its contribution to the coherent wave is further reduced. Therefore, analysis of the interference pattern at the opposite channel face provides information concerning the fuel integrity in situ, providing means of screening reconstituted fuel bundles for quality without the necessity of applying conventional fuel-sipping procedures which are time consuming and expensive.

The coherent scattering inspection method of the invention provides means of detecting and locating faulted or missing fuel rods contained in a regular array inside a thin-walled channel without removing the channel or disassembling the array. The method is amenable to the screening of fuel rod bundles for defects in a rapid and cost effective way that is heretofore unknown to the art. The method of the invention utilizes interference pattern effects, which can be unambiguously interpreted to imply the types and locations of faulted or missing rods in an array. It can be used in conjunction with other techniques that are currently applied to enhance and speed the bundle inspection process.

DETAILED DESCRIPTION OF THE PREFERRED EMBODIMENTS

The method in accordance with the invention will be described with reference to the special case of an 8×8 square array of rods (see FIG. 4) totally immersed in water, which is of interest for nuclear fuel bundles. The fuel bundle depicted in FIG. 4 has a thin-walled channel 2 of generally square cross section, which surrounds the fuel rods 4. One of the fuel rods 4' is shown to be deformed due to swelling. A local area of reduced water density due to radioactive gas (hereinafter referred to as "rad-gas") leaking from the plenum of fuel rod 4' is designated by numeral 6.

Figure 4:
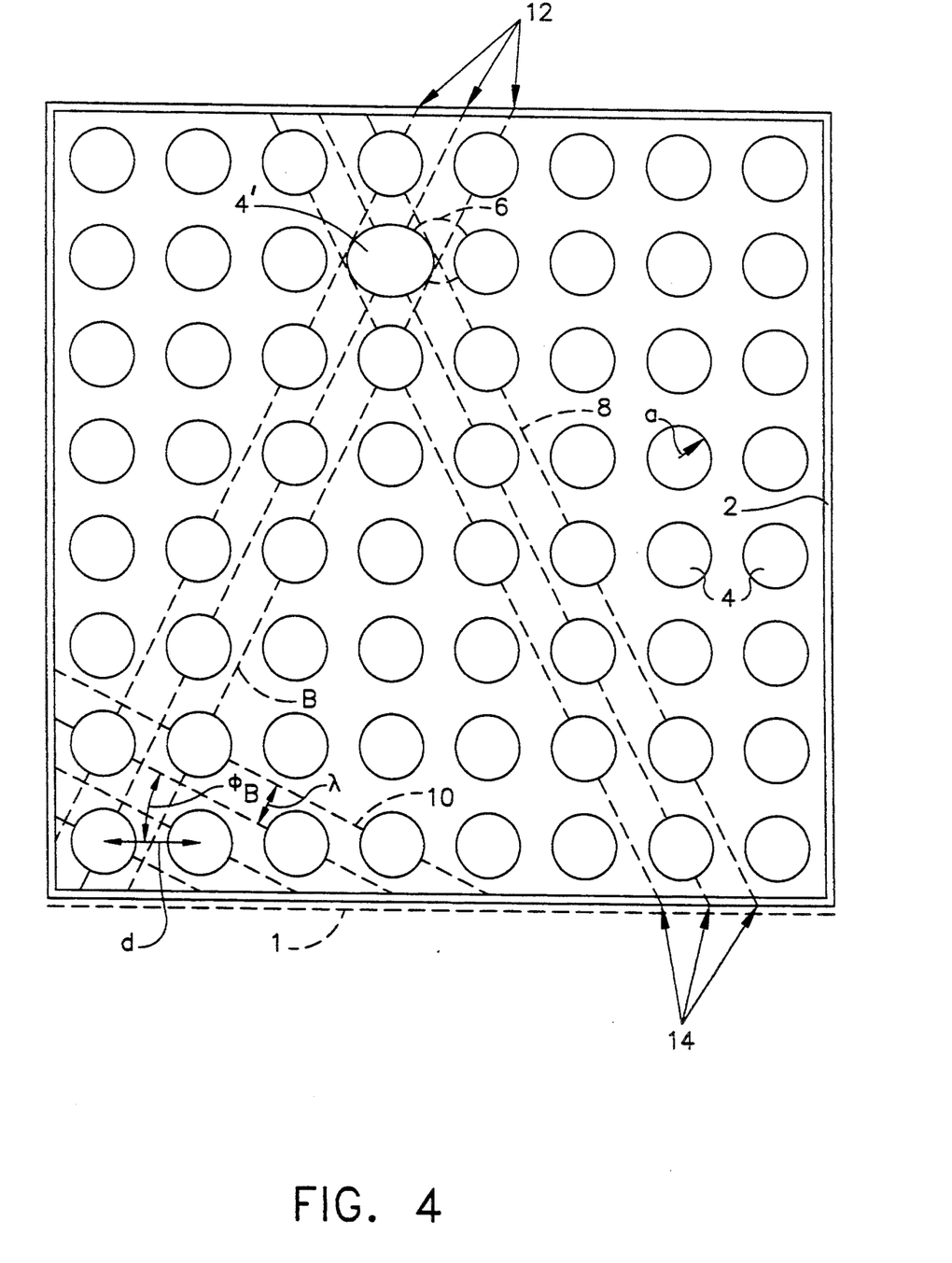
FIG. 4 is a diagram depicting coherent scattering of an incident plane ultrasonic wave by a nuclear fuel bundle.

The dimensions for a typical fuel bundle are: $a=0.2415''$ (6.13 mm), $d=0.64''$ (16.26 mm) and $(d-2a)=0.517''$ (3.99 mm), where $a$ is the rod radius and d is the center-to-center spacing. The area occupied by the rods is a square about 4.96" (126 mm) on a side, which is large compared with ultrasonic wavelengths (typically 16 mm at 100 kHz in water at 160° F.). However, this wavelength is comparable with the inter-rod spacing, so coherent multiple scattering can be important in certain directions for selected frequencies.

Multiple scattering means that each interior rod scatters an incident wave 1 (see FIG. 4) that has been previously scattered by some other rod in the array. The phases of these incident waves are related to the details of the rod spacing. If the rods are not too closely packed and their spacing in some direction is an integral multiple of $2\pi$, then it is possible that some fraction of the rods can cooperate to yield coherent multiple scattering as the incident wave weaves its way through the array. This is a complicated mechanism analytically, but the $N^2$ coherence factor is an intriguing prospect.

Referring to FIG. 4, in response to the incident plane wave 1, a coherently forward-scattered wave front 10 of wavelength $\lambda$ propagates between the rods in the Bragg direction B at a Bragg angle $\Psi_B$. Likewise a coherently back-scattered wave 10 propagates along a second Bragg direction. Bragg scatter and back-scatter observation points are indicated by numerals 12 and 14 respectively in FIG. 4.

Figure 5:
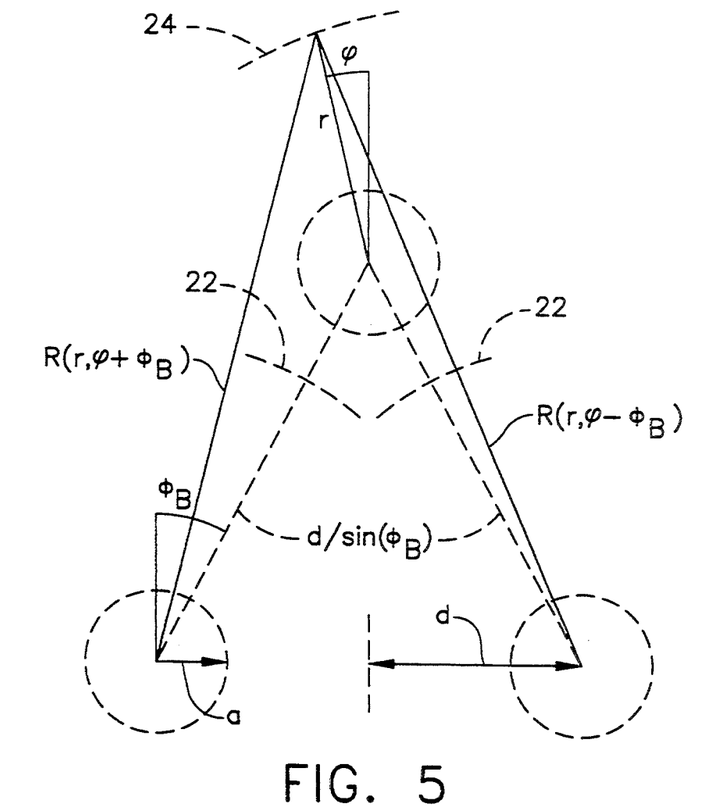
FIG. 5 is a diagram depicting coherent scattering by one rod of a pair of ultrasonic waves propagating along the Bragg directions from two other rods.

As a first step in assessing the interactions of multiple rods in an ultrasonic field, consider the situation depicted in FIG. 5 for identical rods separated by distance d and coherently excited by incident plane waves of frequency f and wavenumber k. The array has a Bragg direction defined by the following parameters:

$$\phi_B = \tan^{-1}\left[\frac{1}{2}\right] \tag{13a}$$

$$\eta = \frac{2\pi a}{d\sin[\phi_B]} \tag{13b}$$

$$f = \frac{c}{d\sin[\phi_B]} \tag{13c}$$

Figure 6:
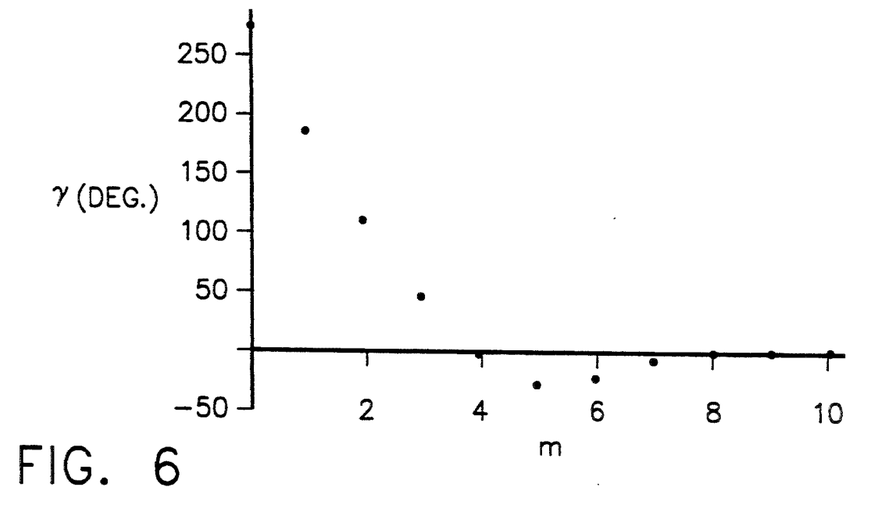
FIG. 6 is a graph of the phase shifts $\gamma_m$ for scattering by a single rod.

The phase shifts $\gamma_m$ for scattering by a single rod are given by Eqs. (11a,b) and shown in FIG. 6 with the phase angle given in degrees.

The low intensity of side-scatter and on-axis forward-scatter for a single rod implies that members of the same row or column of rods do not interact strongly, except for back-scatter. On the other hand, the off-axis forward lobes radiate a sizable portion of the incident wave to alternate row and column rods that form a "diamond" pattern, or sublattice, in a square array. The sides of this repetitive pattern are all in accord with the Bragg condition, so coherence established by the incident plane wave is sustained at each scattering site of the pattern. For 213.2 kHz and the geometry of FIG. 4, the coherent intensity at the third row is calculated from forward-scatter interactions in the first row. This is valid for the leading edge of the wavefront, since coherent contributions from the second row are delayed in time (longer path, or higher multiple of $2\pi$). Rods in row-3 then excite coherent scattering in row-5, and so forth, with the aid of the geometrical relations depicted In FIG. 5. The excitations 22 emanating from the two lower rods are asymptotic cylindrical waves that are in-phase and combine to approximate an incident plane wave at the upper rod, producing the outgoing wave 24. This is only true a few rows from the boundary, where effects of the plane wave excitation are no longer dominant in the outgoing waves.

FIG. 5 suggests that the repeating pattern of cooperating rods results in a recursion rule for the coherent scattering coefficients, row to row. In fact, this can be shown to be the case for the total pressure, radial velocity and intensity. The geometry results in:

$$kR[a, \pm\phi] = \eta\left[1 + \frac{2d\cos(\phi_B \pm \phi)}{a\sin(\phi_B)} + \left(\frac{d}{a\sin(\phi_B)}\right)^2\right]^{\frac{1}{2}} \tag{14}$$

$$kR[r, \pm\phi] = \left[(kr)^2 + \frac{2d(kr)\cos(\phi_B \pm \phi)}{a\sin(\phi_B)} + \left(\frac{d}{a\sin(\phi_B)}\right)^2\right]^{\frac{1}{2}} \tag{15}$$

The first-row scattering coefficients are given by (10) and (11). The coefficients for row-3 rods are:

$$B_m(\phi) = -A_m \frac{H'_m(kR[a, \phi]) + H'_m(kR[a, -\phi])}{H'_m(\eta)}$$
$$- \epsilon_m i^m \frac{J'_m(kR[a, \phi]) + J'_m(kR[a, -\phi])}{H'_m(\eta)} \tag{16}$$

Each succeeding row has coefficients that are computed from Eq. (16). A rod in the j-th row has the coefficients:

$$C_m^{(j)}(\phi) = \tag{17}$$

$$-B_m(\phi)\left[1 + \left(\frac{H'_m(kR[a,\phi]) + H'_m(kR[a,-\phi])}{H'_m(\eta)}\right)^{\frac{j-3}{2}}\right]$$

for j=5, 7, 9 . . . Note that the B and C coefficients are functions of $\Psi$, since the rods have finite radius and the incident waves are not perfectly plane.

The scattered wave pressure and radial velocity are:

$$p_s^{(j)}(r,\phi) = P_0 \sum_{m=0}^{\infty} C_m^{(j)}(\phi)\cos(m\phi)H_m(kr) \quad (18)$$

$$u_s^{(j)}(r,\phi) = -i\frac{P_0}{\rho c} \sum_{m=0}^{\infty} c_m^{(j)}(\phi)\cos(m\phi) C_m^{(j)}(\phi) H'_m(kr) \quad (19)$$

and the incoming wave pressure and radial velocity are:

$$p_i^{(j)}(r,\Psi) = p_s^{(j-2)}(kR[r,\Psi],\Psi) + p_i^{(j-2)}(kR[r,\Psi],\Psi) + \\ p_s^{(j-2)}(kR[r,-\Psi],-\Psi) + p_i^{(j-2)}(kR[r,-\Psi],-\Psi) \quad (20)$$

$$u_i^{(j)}(r,\Psi) = u_s^{(j-2)}(kR[r,\Psi],\Psi) + u_i^{(j-2)}(kR[r,\Psi],\Psi) + u_s^{(j-2)}(kR[r,-\Psi],-\Psi) + u_i^{(j-2)}(kR[r,-\Psi],-\Psi) \quad (21)$$

The point (r, $\Psi$) is referenced to the center of a rod in the j-th row. The total intensity at this point is a superposition of the scattered and incident waves.

$$I^{(j)}(r,\Psi) = \tfrac{1}{2} Re\{[p_s^{(j)}(r,\Psi) + p_i^{(j)}(r,\Psi)][u_s^{(j)}(r,\Psi) + u_i^{(j)}(r,\Psi)]\} \quad (22)$$

This intensity illuminates rods in the (j+2)-th row, etc. In this way, the coherent intensity at the opposite face of the array is built up by multiple scattering events. Clearly, the intensity at any given rod in a row is a function of the past scattering events in its propagation path. The more scatterers there are, the narrower and more peaked the intensity distribution becomes.

Figure 7:
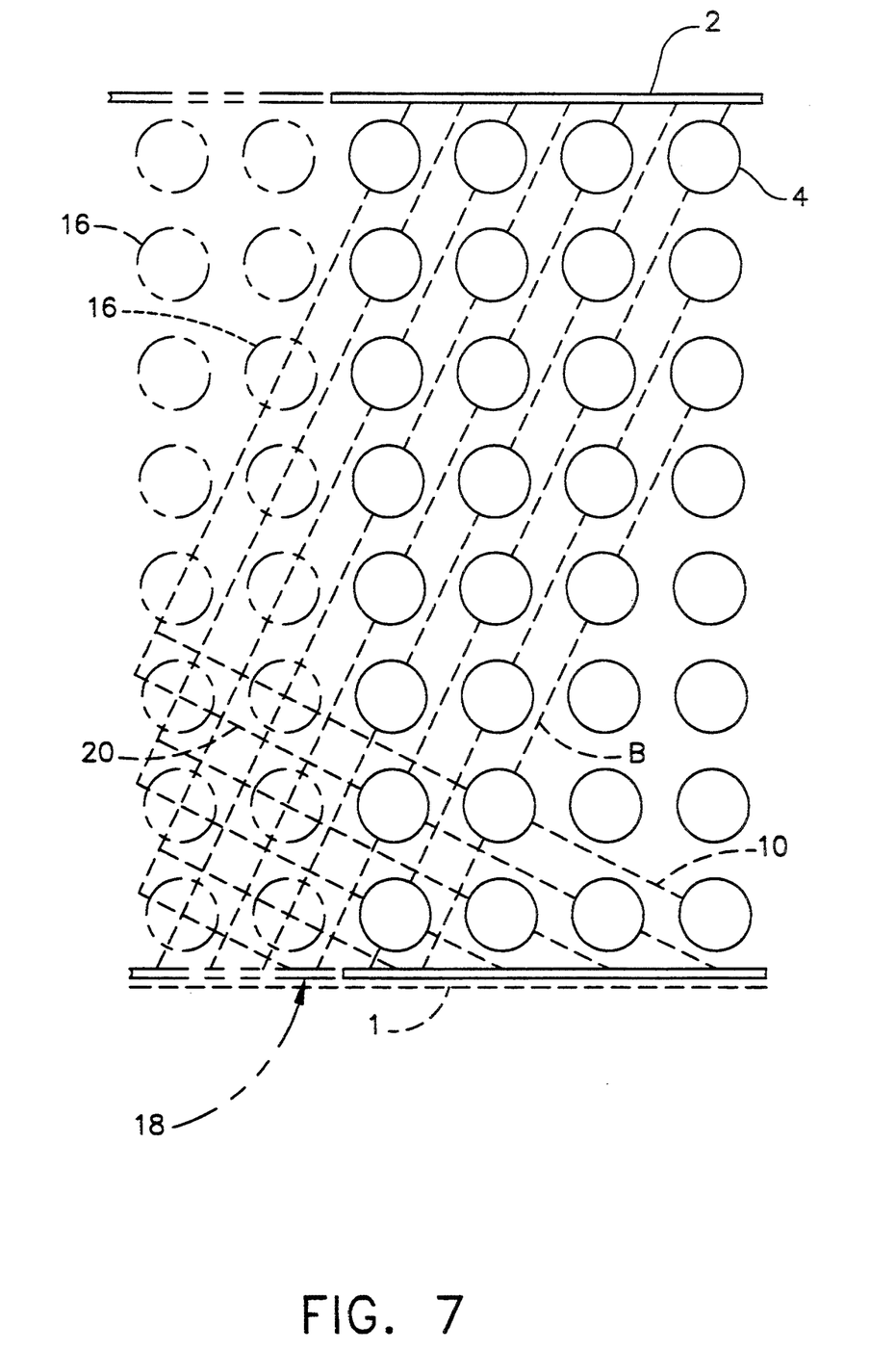
FIG. 7 is a diagram depicting the edge effects for coherent scattering of an incident plane ultrasonic wave by a nuclear fuel bundle.

Edge effects are a function of the channel-box dimensions and spacing relative to the rod spacing. In the ideal case, reflections from the inner surfaces of the channels reinforce the scattering process in the proper phase relationship to make j the same, even near the edges. Channel bowing, skew, etc. will reduce the effective value of j and diminish the coherence over part of the array. Otherwise, the channels act as imperfect mirrors for the ultrasound, essentially extending the array by forming images beyond the physical boundaries of the bundle. Edge effects are illustrated schematically in FIG. 7, wherein 16 denotes the rod images, 18 denotes the channel image and 20 denotes the reflected wave front.

In the Bragg directions for FIG. 5, the intensity is not just twice that of a single scatterer, but four times as large for ideal conditions. This is the $N^2$ affect alluded to above, and it applies regardless of the number of rods in the array, as long as they are coherently excited by the incident wave and there is negligible attenuation in the medium. If the Bragg condition is not satisfied exactly, then the $N^2$ factor is reduced. This results in rapid oscillations with angle in the phase-factor, leading to complicated interference effects, which tend to cancel each other in intensity. Therefore, on the average, the scattering is incoherent for all angles, except near the Bragg directions.

Evidently, the intensity in a Bragg direction would be high, compared to the background, if all N rods were excited simultaneously by a single plane wave. This would be the case for a linear array impacted normally by a plane wave "tone-burst" of the proper frequency and duration. The intensity peaks would be sensitive to the number of scatterers that cooperate to form the Bragg diffraction. For example, for an 8×8 linear array in which one rod was not "cooperating", the Bragg peaks would be reduced by about 50% from the ideal case. Two recalcitrants would reduce the peaks 75%. Therefore, Bragg-diffraction peak amplitude is sensitive to non-cooperating scatterers.

If all rods in a linear array are excited simultaneously and the Bragg peaks in two directions are measured, it is possible to determine which of the rods are not cooperating, if any. The symmetry of the peaks can be used to uniquely identify those rods which scatter incoherently. Since a two-dimensional array is a super-position of linear arrays, the same symmetry arguments apply. Thus, the pattern of coherent peaks on two faces of the channel boxes can be used to triangulate each faulty rod. There is no need to remove the boxes; indeed, they assist in the inspection procedure by acting like ultrasonic mirrors.

Figure 8:
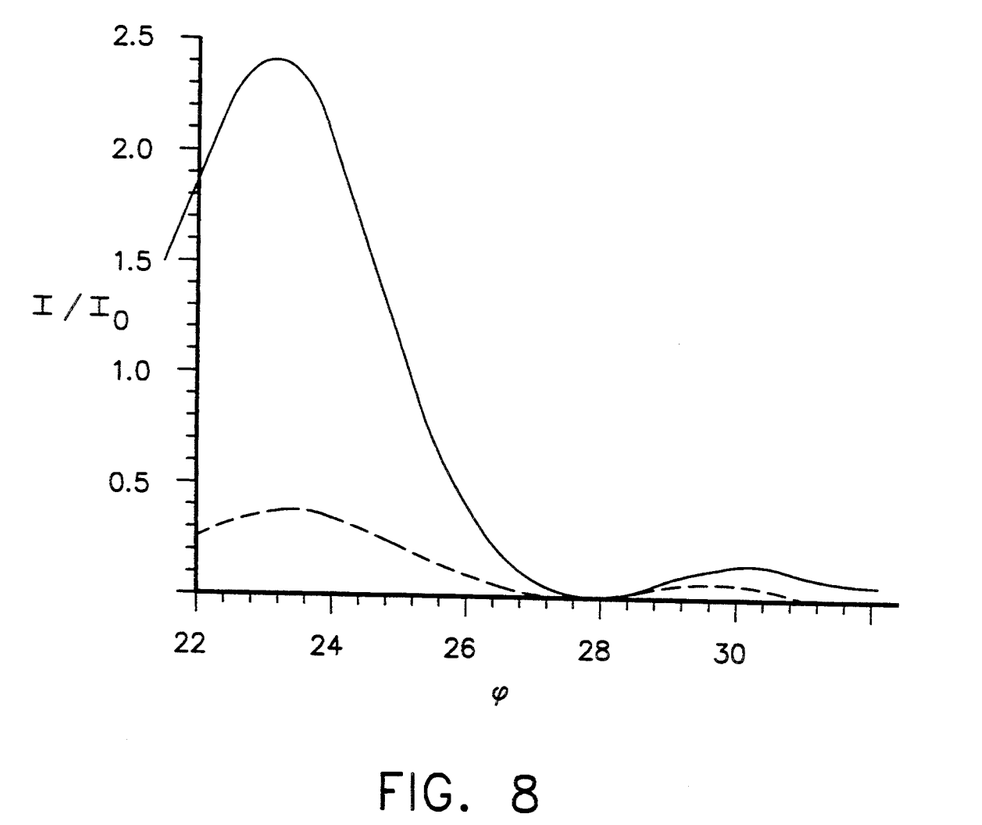
FIG. 8 is a graph of the coherent intensity distribution for an 8×8 array with (dashed curve) and without (solid curve) attenuation due to rad-gas leakage.

The coherent intensity distribution for an 8×8 array (j=7) is shown in FIG. 8 for the dimensions given above. The peak is a bit offset from the ideal Bragg angle (26°), and its amplitude is not a simple function of N. This is a result of blocking effects by the finite rod size and the relatively close spacing.

This coherent wavefront interference pattern is repeated regularly across the opposite-side channel face. For a short-duration, narrow-band "tone-burst" excitation, the pattern occurs at a time determined by the zig-zag path of the scattered wavefront propagating through the bundle. There are shorter propagation paths for the incoherent waves, but their intensity is much lower than the peak in FIG. 8. The incoherent intensity is of the order of the secondary peak, occurring at about 30° in FIG. 8.

The most important factors in breaking the symmetry required for spatial coherence are: 1) variations in spacing d from rod-to-rod; 2) poor coupling of the rod surface to the liquid medium in which the scattering takes place; 3) attenuation due to scattering and/or absorption in the path of propagation; and 4) poor special quality of the incident wave. Assuming that 1) and 4) can be managed by design, 2) and 3) would be the culprits that might be indicative of fuel rod defects. For example, rad-gas leaking from a significant fissure in a rod in the array might change the local water density sufficiently that the acoustic impedance would increase. This would perturb the ability of one, or more, of the adjacent rods to cooperate efficiently in the scattering process. If a fissure were sufficiently large, water ingress could lead to swelling of the ruptured rod, thereby changing the radius and perturbing the scattering coefficients for that particular rod. However, "pin-hole" leaks would probably not result in significant incoherence effects and would go undetected.

If one side of the channel were excited between rod spacers with a narrow-band plane wave of the proper wave-vector (i.e., frequency and direction), then the coherent peaks are detectable at the other channel faces in a regular pattern at a specific time after excitation. The coherent scattering peaks should be uniform, except for predictable edge effects. Anomalous peaks result from a leaking fuel rod and the rad-gas concentration near it.

The forward-, back- and side-scatter are also correlated in the Bragg directions because they are excited by the same incident wave. The location of the anomalous peak on different faces provides means of triangulating the leaking rod location, approximately. Every rod in the array can be accessed by the incident plane wave from the various channel faces.

A bundle could contain more than one defective rod. If so, peaks on a channel face in other directions would show anomalous heights, and the other leakers could be detected and located by the same method as for a single faulted rod. It should be clear that rad-gas effects are not fully localized, so peak attenuation will identify the neighborhood of the leaker, at best. This is often all that is necessary for quality control purposes.

The rod spacing may vary somewhat, introducing some degree of incoherence that would reduce the Bragg effect. This should be discernible in the nature of the data; i.e., such effects should not be localized to any given rod, in general. In the event that a single rod is substantially out of line in the array, but not a leaker, then the data could be interpreted to suggest a failed rod spacer or a bowed fuel rod. In either event, corrective action would be indicated. Therefore, the method should be sensitive to various fuel bundle anomalies.

Figure 9:
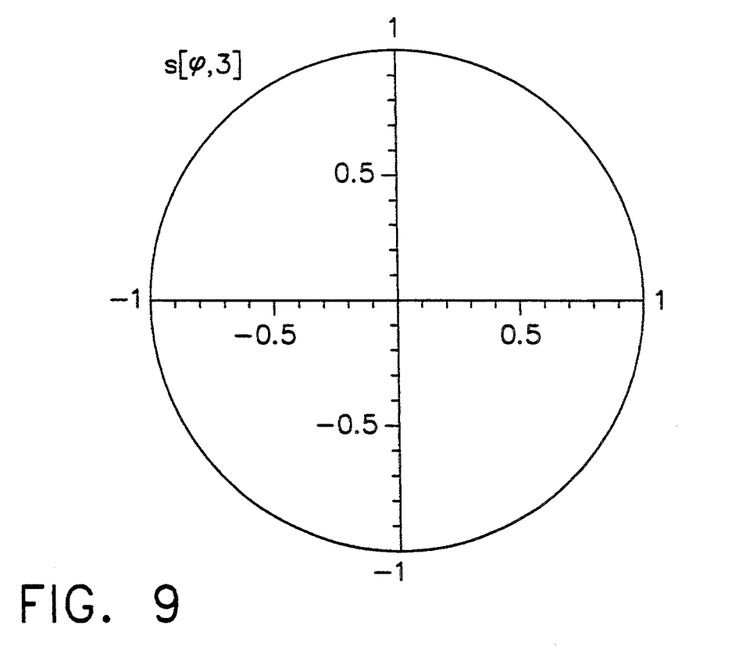
FIG. 9 is a graph of the attenuation factor for no leakage at row-3 of a nuclear fuel bundle.
Figure 10:
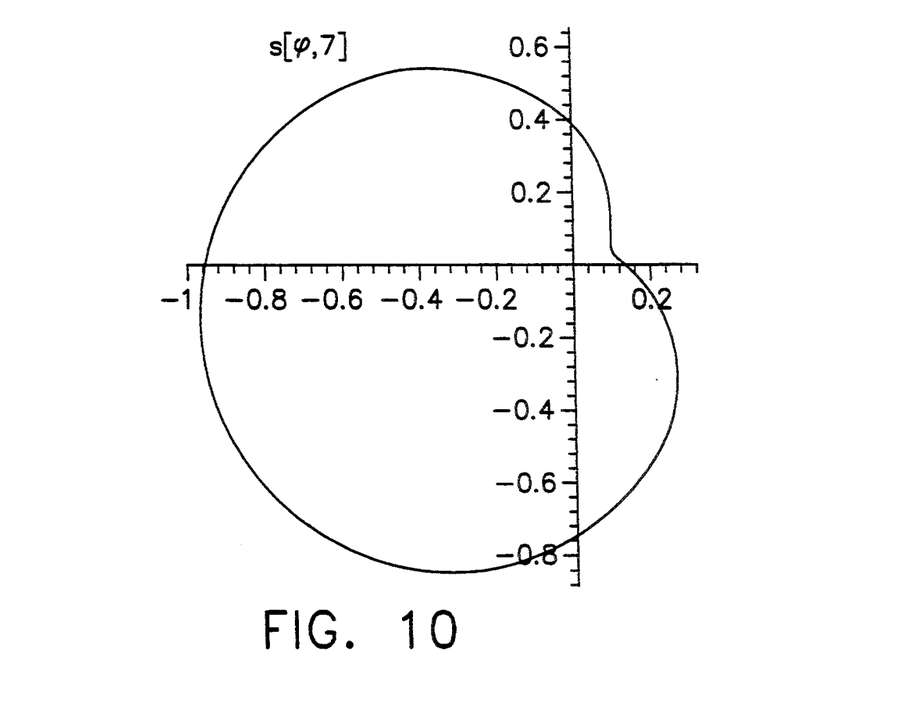
FIG. 10 is a graph of the attenuation factor for leakage at row-7 of a nuclear fuel bundle.

To examine the effects of rad-gas concentrated about a particular rod, an attenuation factor $s[\Psi,j]$ is applied to the intensity. FIG. 9 shows the factor for no leakage at row-3. This is the same for members of all rows, except row-7, where a leaker is hypothesized. The attenuation factor is assumed to be:

$$s[\phi,j] = \left[\frac{1 - a_0\cos(\phi - \phi_0)}{1 + a_0}\right]\delta_{j,j'} \quad (23)$$

where the Kronecker-delta is unity when $j=j'$ and zero otherwise. In this case, $j'=7$, $\Psi_0=23°$ and $a_0=0.8$, by assumption. The attenuation at the leaker then looks like FIG. 10.

This distribution assumes that the rad-gas concentration is highest in the first quadrant and negligible in the third quadrant. The incident and outgoing pressure waves are affected differently by this factor, depending on their directions, with the result shown in FIG. 8.

The solid curve is half of the coherent signal peak for a path of non-leakers. The dashed curve is the attenuated signal resulting from a single leaker in the scattering path. This signal pattern is repeated across the face of the channel. Evidently, the overall effect of the rad-gas is a sizable reduction of at least one coherent peak, perhaps driving it into the incoherent background. Therefore, one or more peaks in the pattern could appear to be missing entirely, because of concentrated rad-gas bubbles from leakers.

As mentioned above, when viewed from different faces, the relative position of the attenuated peak(s) changes, providing means for triangulating the position of the leaker(s). The relative heights of the reduced peaks is about the same, if above background. However, the degree of reduction from the unattenuated peaks depends on the scattering and absorption (i.e., total attenuation) of the ultrasound by the local rad-gas concentration, The detection method of the invention can be carried out using conventional ultrasonic transducers, e.g., linear arrays of ultrasonic transducers. The incident plane wave can be generated by simultaneously activating one bank of transducers at one channel face and then detecting the multiple-scattered wave at the opposing face with a second bank of transducers. To triangulate the position of a "leaker", the process can be repeated at the other pair of opposing channel faces.

The bank of detecting transducers will provide outputs indicative of the intensity of the multiple-scattered wave across the channel face. This pattern can be compared to a reference pattern acquired by inspection of a standard bundle free of defects. Any significant discrepancy between the patterns may indicate a missing or misaligned fuel rod in the bundle.

Alternatively, the bundle can be inspected both before installation in and after removal from the reactor core. Any significant discrepancy between the respective Bragg scattering patterns may indicate a change in structure caused by the reactor environment, such as a "leaker" or other defect.

There is a "probability of detection" associated with the method which depends on the type of leakers encountered and other variables of a practical nature that have to be determined empirically. If used in conjunction with other techniques that are more time-consuming and expensive to apply, coherent ultrasonic scattering techniques play an important role in reducing costs of locating major fuel rod leaks.

The preferred embodiments have been disclosed for the purpose of illustration only. Variations and modifications of those embodiments will be readily apparent to engineers of ordinary skill in the art of ultrasonic detection. Specifically, the invention has application to inspection of reconstituted fuel bundle assemblies and/or in situ screening of fuel bundles for leaks during BWR or PWR plant refueling processes. However, the method is readily applicable to inspection of any generic array of rods of a wide variety of shapes (e.g., square, rectangular or circular), submerged in a sound-conducting medium such as water, in which the variations in rod position and dimensions are small relative to the ultrasonic wavelength. All such variations and modifications are intended to be encompassed by the claims appended hereto.

We claim:

1. A method for ultrasonic inspection of a closely packed regular array of mutually parallel, uniformly sized and spaced rigid rods immersed in a compressible medium, said parallel rods having a longitudinal axis, comprising the steps of:

transmitting a first plane, monochromatic ultrasonic wave toward said array of rods on one side thereof, said ultrasonic wave propagating through said array in a direction which is not parallel to said longitudinal axis of said parallel rods; and detecting a first interference pattern produced on a side of said array opposing said one side as the result of multiple scattering and diffraction of said first plane ultrasonic wave during propagation through said array.

2. The method as defined in claim 1, wherein said detecting step comprises detecting the amplitude of the interference pattern at points where an intensity peak due to coherent multiple scattering of said first plane ultrasonic wave by a standard array of rods is expected.

3. The method as defined in claim 1, wherein each of said rods has a generally circular cylindrical shape, said array of rods is a square array with the centers of adjacent rods separated by a distance d, and said first plane ultrasonic wave is a tone burst having a frequency:

$$f = \frac{c}{d\sin[\phi_B]}$$

where $\Psi_B$ is the Bragg angle and c is the speed of sound.

4. The method as defined in claim 1, wherein said rods of said array are arranged in a plurality of mutually parallel rows, said first plane ultrasonic wave being substantially parallel to said rows.

5. The method as defined in claim 1, wherein said sequence of transmitting and detecting steps is repeated to produce a second interference pattern, further comprising the step of comparing said first and second interference patterns.

6. The method as defined in claim 1, further comprising the step of comparing said first interference pattern to a standard interference pattern produced by inspection of a standard array of rods arranged in the same way and shaped the same as the rods of said array being inspected, except that said standard array of rods is free of defects.

7. The method as defined in claim 1, further comprising the steps of:
transmitting a second plane, monochromatic ultrasonic wave toward said array of rods on a side adjacent to said one side thereof; and
detecting a second interference pattern produced on a side of said array opposing said adjacent side as the result of multiple scattering and diffraction of said second plane ultrasonic wave during propagation through said array; and
determining the location of a defective rod by triangulation using said first and second interference patterns.

8. The method as defined in claim 1, wherein said array of rods is surrounded by a generally square-shaped thin-walled channel having first through fourth planar channel faces, said third channel face opposes said first channel face, said fourth channel face opposes said second channel face, said first plane ultrasonic wave impinges on said first channel face with its wavefront in parallel therewith, and said first interference pattern is detected at said third channel face.

9. The method as defined in claim 7, wherein said array of rods is surrounded by a generally square-shaped thin-walled channel having first through fourth planar channel faces, said third channel face opposes said first channel face, said fourth channel face opposes said second channel face, said first plane ultrasonic wave impinges on said first channel face with its wavefront in parallel therewith, said first interference pattern is detected at said third channel face, said second plane ultrasonic wave impinges on said second channel face with its wavefront in parallel therewith, and said second interference pattern is detected at said fourth channel face.

10. An apparatus for ultrasonic inspection of a closely packed regular array of mutually parallel, uniformly sized and spaced rigid rods immersed in a compressible medium, said parallel rods having a longitudinal axis, comprising:
means for transmitting a plane, monochromatic ultrasonic wave toward said array of rods on one side thereof, said ultrasonic wave propagating through said array in a direction which is not parallel to said longitudinal axis of said parallel rods; and
means for detecting an interference pattern produced on a side of said array opposing said one side as the result of multiple scattering and diffraction of said plane ultrasonic wave during propagation through said array.

11. The apparatus as defined in claim 10, wherein each of said rods has a generally circular cylindrical shape, said array of rods is a square array with the centers of adjacent rods separated by a distance d, and said first plane ultrasonic wave is a tone burst having a frequency:

$$f = \frac{c}{d\sin[\phi_B]}$$

where $\Psi_B$ is the Bragg angle and c is the speed of sound.

12. The apparatus as defined in claim 10, wherein said rods of said array are arranged in a plurality of mutually parallel rows, said first plane ultrasonic wave being substantially parallel to said rows.

13. The apparatus as defined in claim 10, wherein said array of rods is surrounded by a generally square-shaped thin-walled channel, said plane ultrasonic wave impinges on a first channel face of said channel with its wavefront in parallel therewith, and said interference pattern is detected at a channel face opposing said first channel face.

14. The apparatus as defined in claim 13, wherein said transmitting means comprises a first linear array of ultrasonic transducers coupled to said first channel face and said detecting means comprises a second linear array of ultrasonic transducers coupled to said channel face opposing said first channel face.

* * * * *